Figure 1A:
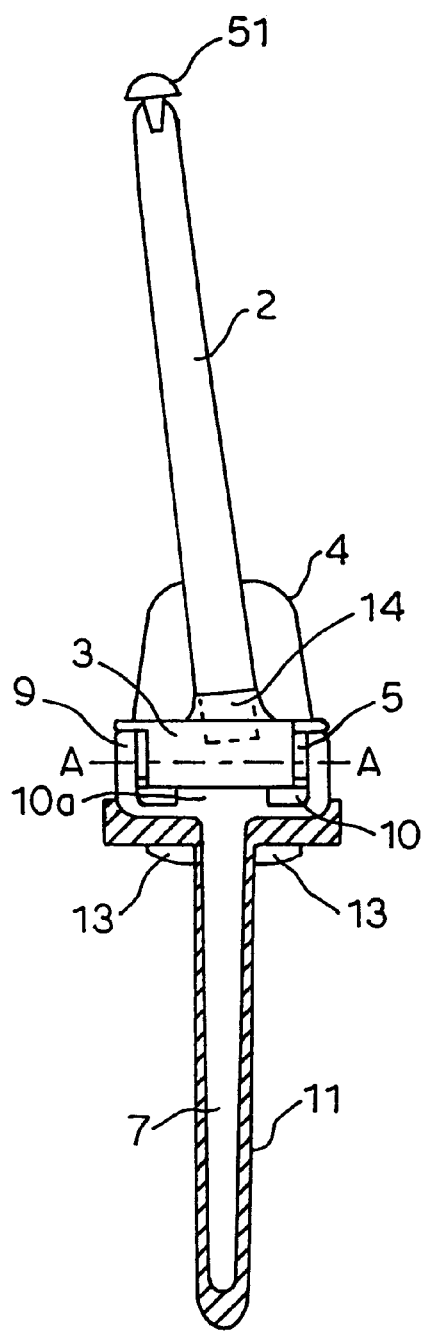

United States Patent [19]
Walker

[11] Patent Number: 6,019,794
[45] Date of Patent: Feb. 1, 2000

[54] TOTAL KNEE REPLACEMENT PROSTHESIS

[75] Inventor: Peter Stanley Walker, Stanmore, United Kingdom

[73] Assignee: University College London, London, United Kingdom

[21] Appl. No.: 08/513,979

[22] PCT Filed: Mar. 15, 1994

[86] PCT No.: PCT/GB94/00512

§ 371 Date: Feb. 28, 1996

§ 102(e) Date: Feb. 28, 1996

[87] PCT Pub. No.: WO94/21198

PCT Pub. Date: Sep. 29, 1994

[30] Foreign Application Priority Data

Mar. 15, 1993 [GB] United Kingdom .................... 9305279

[51] Int. Cl.⁷ ......................................................... A61F 2/38
[52] U.S. Cl. .............................................................. 623/20
[58] Field of Search ................................................. 623/20

[56] References Cited

U.S. PATENT DOCUMENTS

| | | |
|---|---|---|
| 4,136,403 | 1/1979 | Walther et al. . |
| 4,136,405 | 1/1979 | Pastrick et al. . |
| 4,262,368 | 4/1981 | Lacey . |
| 4,301,553 | 11/1981 | Noiles . |
| 4,822,366 | 4/1989 | Boleksy .................................... 623/20 |
| 5,370,701 | 12/1994 | Finn ........................................ 623/20 |

FOREIGN PATENT DOCUMENTS

| | | |
|---|---|---|
| 0376658 | 7/1990 | European Pat. Off. . |
| 0378928 | 7/1990 | European Pat. Off. . |
| 0420460 | 4/1991 | European Pat. Off. . |
| 1514479 | 6/1978 | United Kingdom . |
| 1553836 | 10/1979 | United Kingdom . |
| 8503425 | 8/1985 | WIPO . |
| 8906947 | 8/1989 | WIPO . |

*Primary Examiner*—David H. Willse
*Attorney, Agent, or Firm*—Moore & Van Allen, PLLC

[57] ABSTRACT

A total knee replacement prosthesis (TKR) is provided in which a pintle hinge enables the knee to pivot about a horizontal axis. A degree of rotational movement about a vertical axis is provided by fabricating the tibial component in at least two parts. One part is attached to the hinge and includes a stem portion which is designed to be rotatable with a hollow shell adapted to be fixed into the tibia. The hinge portion is standardized and is designed to receive femoral and tibial stem portions having dimensions to suit a particular patient.

11 Claims, 4 Drawing Sheets

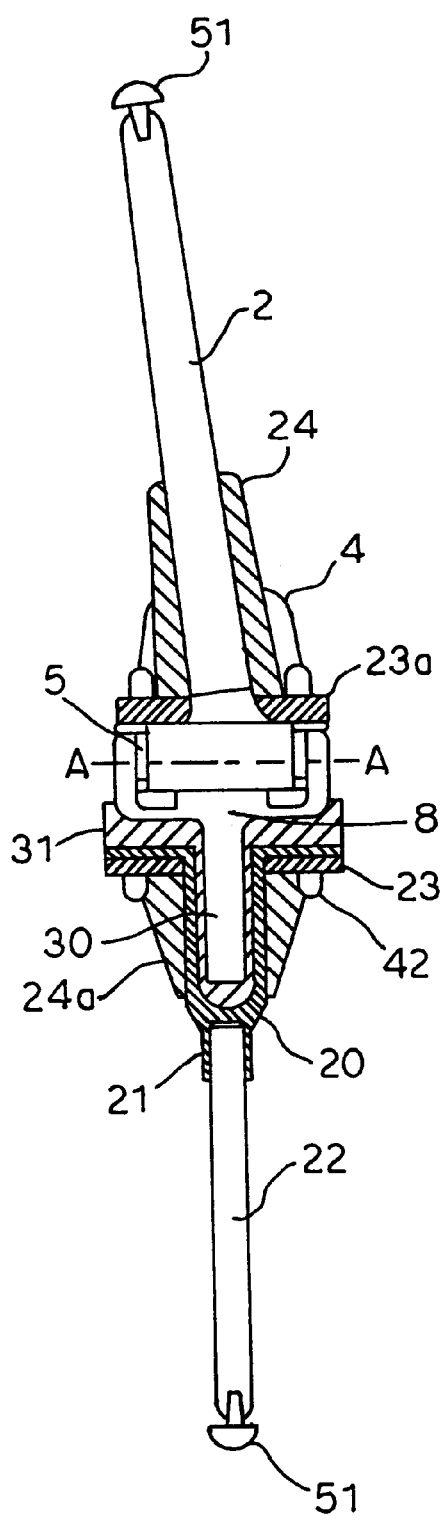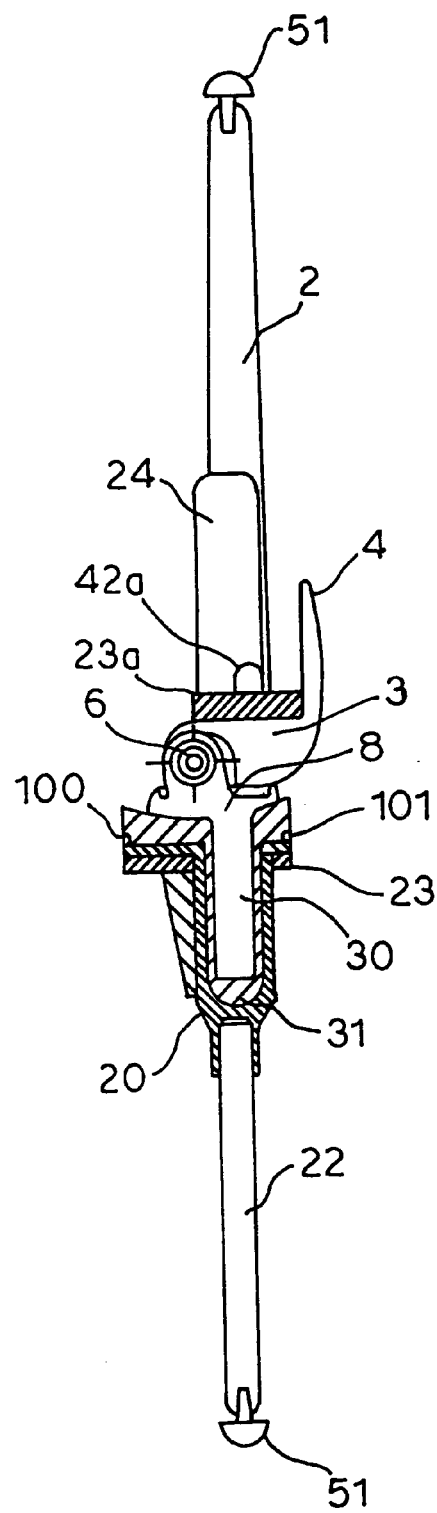
FIG. 2A    FIG. 2

TOTAL KNEE REPLACEMENT PROSTHESIS

This invention relates to a total knee replacement prosthesis (hereinafter called TKR) and, in particular, to a TKR which is constructed in a modular system so that additional components can be added to deal with particular problems of the natural knee.

TKR is called for in cases where the natural knee exhibits severe instability, where failure of a previously inserted TKR has resulted in further loss of bone, or where a large amount of bone is to be removed and replaced, perhaps because of cancer.

According to one aspect of the present invention there is provided a total knee replacement prosthesis (TKR) which comprises a femoral component which is pivotably connected to a tibial component at a hinge for pivoting movement, about a lateral-medial axis, at least one of the components being received within a bearing component adapted to be inserted in an intramedullary canal, so that the component is rotatable within the bearing component to provide a degree of rotational freedom of movement for the prosthesis, the femoral component comprising a stem portion fixedly attached by attachment means to said hinge, said attachment means being standardised so that a stem of desired size can be selected for a particular patient.

In general, the tibial and femoral components are constructed from a metal which is biomedically inert, e.g. a stainless steel, cobalt-chromium-molybdenum alloy or titanium alloy. The bearing components should preferably exhibit low friction with respect to the component which rotates within them and typically materials which meet this requirement are polyolefines or nylons. Particularly preferred materials for this purpose are ultra-high molecular weight polyethylenes. Preferably, the rotational movement takes place by rotation of a tibial stem within a tubular or hollow bearing component which is fixed relatively to the tibia. Thus, for example, the tibial component may comprise a spigot which is secured at one end to a part of the hinge and at the other is received by a bearing component. The bearing component may have an internal canal dimensioned to receive the tibial spigot and an external surface suitably sized to fit the bone canal. Lugs may be formed on the outer surface of the tibial bearing component in order to prevent rotation of the plastic bearing component in the bone canal.

In a preferred construction, the tibial and femoral components are pivotably connected by a pintle hinge. Such a hinge has a pin which passes through aligned bores in the two components. Conveniently, the femoral component includes a body portion which has a bore to receive the hinge pin and the tibial component includes a pair of ears or lugs which extend on each side of the body portion of the femoral component. The pin is preferably removably fixed by suitable locking means, such as circlips in apertures in the ears, and includes plastics bushes to facilitate pivoting of the hinge pin in the bore of the body portion and to avoid metal to metal contact. Thus, the femoral and tibial components can be installed in their relevant intramedullary canals and the joint made by introducing the pin and the locking means.

In order to provide further control over the movement of the joint, a plastic bearing plate or bumper component may be introduced in the area of the hinge between the tibial component and the femoral component to provide a stop at the limits of extension of the joint. This plate or bumper is preferably formed with a concave upper surface so as to provide an additional bearing surface to the hinge joint, i.e. additional to the plastics bushes. The plastic bumper may be a snap fit into a recess in the upper part of the tibial plate so as to be replaceable if worn or for adjustment of the hinging movement of the prosthesis.

In cases where it is desired to provide a tibial component which is longer or shorter than a standard size or a stem of special profile or thickness is required, the plastic bearing component is made shorter and can be fitted within a metal shell component. The metal shell component is provided with a socket at its distal end into which modular tibial stems having a range of diameters and lengths can be fitted. Similarly, where it is desired to provide a femoral component which differs from a standard size, the femoral hinge component or a shell which fits over the hinge component is formed with a socket at its proximal end into which modular femoral stems having a range of diameters and sizes can be fitted to provide a TKR uniquely suited for a particular patient.

Similarly, in the case where larger amounts of bone than usual are to be removed by the surgeon, either space filler components can be provided which are preferably manufactured from ultra-high molecular weight polyethylene and slid over the tibial or femoral component stems or metal extension shafts could be provided.

Figure 1:
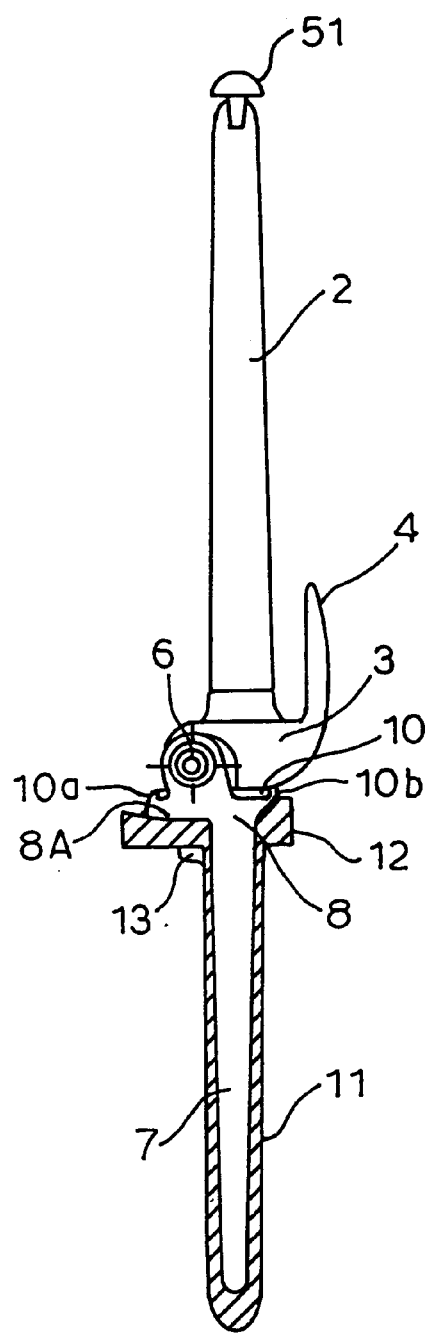
Figure 3A:
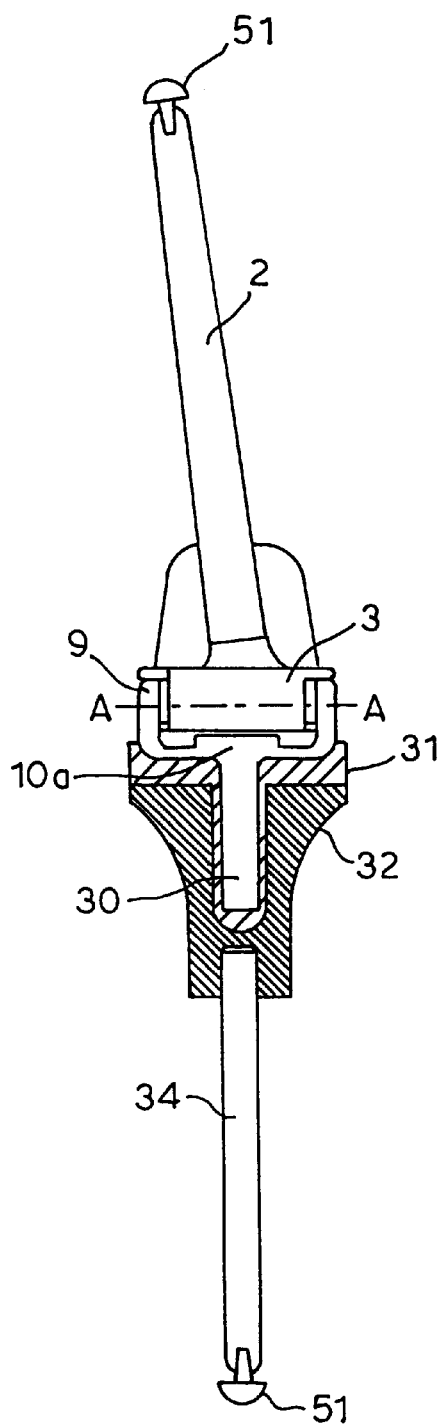
Figure 3:
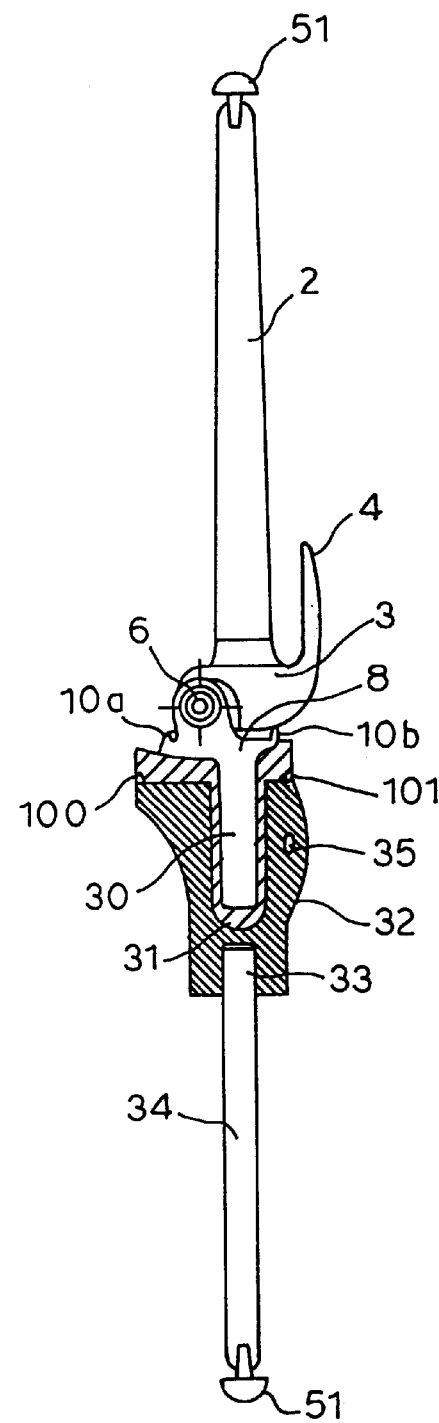
Figure 4:
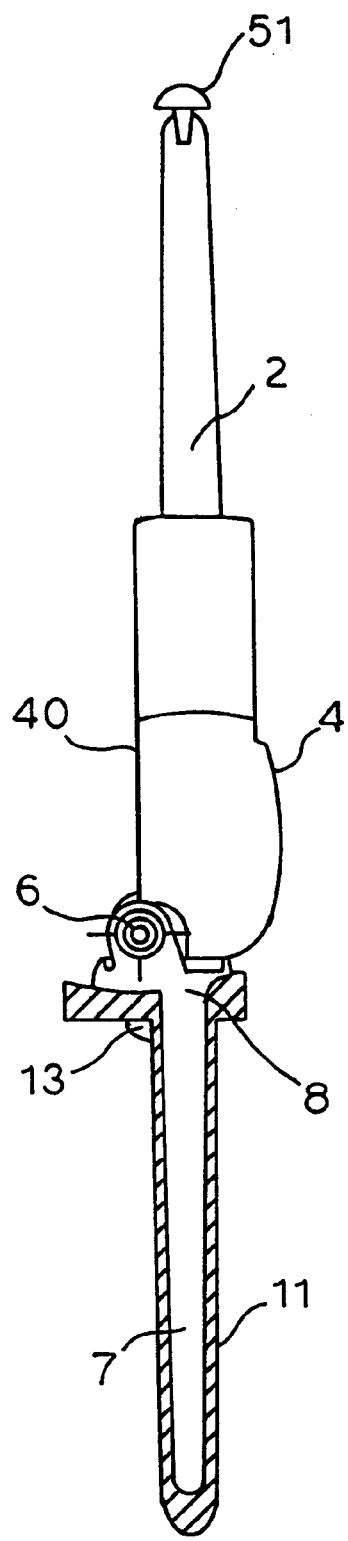
Figure 4A:
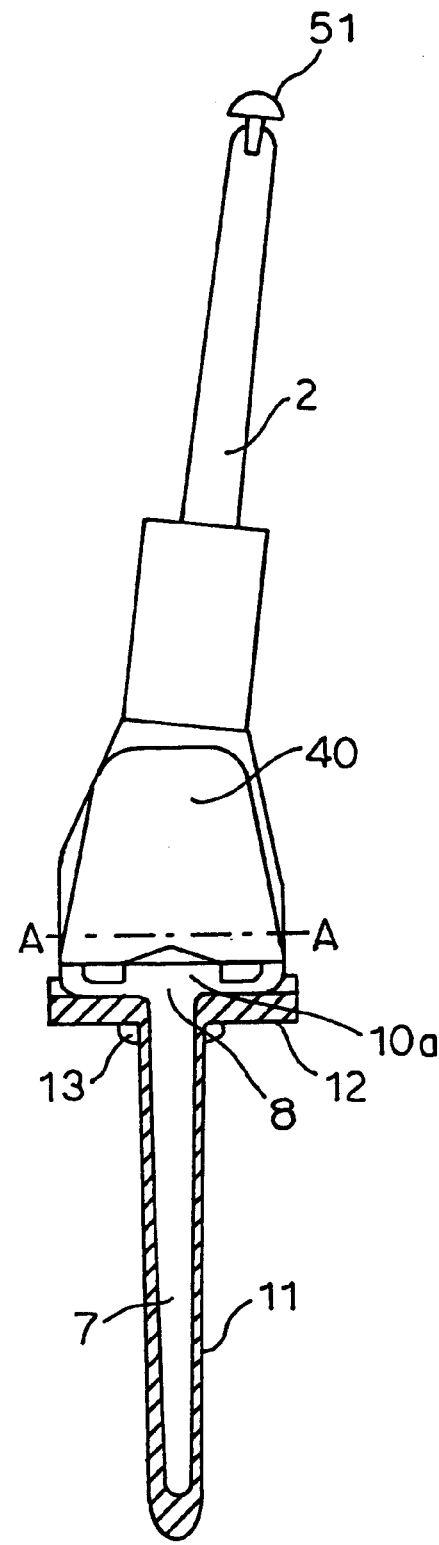

The present invention is illustrated by the following description and accompanying drawings, in which:

FIG. 1 is a medial view of a first embodiment of a TKR in accordance with the invention, FIG. 1A is a posterior view of the same embodiment, FIG. 2 is a view similar to FIG. 1 of a second embodiment, FIG. 2A is a posterior view of the embodiment shown in FIG. 2, FIG. 3 is a view similar to FIG. 1 of a third embodiment in accordance with the invention, FIG. 3A is a posterior view of the TKR shown in FIG. 3, FIG. 4 is a view similar to FIG. 1 of a fourth embodiment, and FIG. 4A is an anterior view of the TKR shown in FIG. 4.

Referring to FIGS. 1 and 1A, the TKR in accordance with the invention comprises a femoral component 1, comprising a femoral stem 2, which is fixedly attached to a femoral hinge component 3. As shown in FIG. 1A, the stem component 2 makes an oblique angle with the lateral/medial line A—A of the hinge. The precise angle which the stem makes with the axis A—A depends on whether the prosthesis is for a left or right leg and the particular formation of the joint of the patient. The femoral hinge component 3 includes a patellar flange 4, which is shaped to conform with a standard plastic patellar button, e.g. of the Kinemax type.

The femoral hinge component 3 is formed with a bore 5 for receiving two ultra-high molecular weight polyethylene bushes (not shown) and a hinge pin 6.

The tibial component comprises a tibial stem 7 and at its proximal end a tibial hinge part 8. The tibial hinge part 8 is formed with a pair of ears 9 which are pierced to receive the respective ends of the pin 6 and are secured by removable circlips (not shown).

Located between the corresponding surfaces of the femoral and tibial hinge parts 3 and 8 is a plastics bumper 10. The plastics bumper 10 is a snap-fit in a recess formed in the top plate of tibial hinge component 8 and its upper surface has a concave form corresponding to the outer surface of hinge component 3. Thus, when the joint is placed under flexion by pivoting about the axis A—A, there is a tendency to provide an additional bearing surface to prolong the life of the joint and to provide a stop at extreme points of movement. The recess in which the plastic bumper 10 is received includes abutments 10a and 10b in the anterior and posterior locations which have a length and height sufficient to prevent the bumper twisting out of the recess under extreme torque.

The tibial stem component 7 is received within a tibial bearing component 11 which has a tubular portion for insertion into the intramedullary canal of the tibia and a proximal portion 12 providing a bearing support for the tibial hinge component 8. As can be seen from the drawing, the bearing component 12 and the tibial hinge component 8 have corresponding curved surfaces 8A in the plane at right-angles to the axis A—A. Stem 7 is rotatable within the bearing component 11 to at least some degree, to provide rotational laxity. The upper surface of the bearing component 12 is shaped so that there is a tendency for the component 8 to return to the 'in-line' position after a twisting force is removed. The tibial bearing component includes lugs 13 to prevent rotation of the component 12 and 11 in the canal. The stem 2 preferably includes at its distal end a spigot 14 for attachment to the hinge component 3. Preferably, the attachment is by press-fitting or by heat-shrinking. In this way, a customised stem can be selected for a patient after inspection of an X-ray of his knee and a femoral stem of suitable size attached to the hinge component. As a result, the surgeon is supplied with a prosthesis which has been assembled for his particular patient.

Referring to FIGS. 2 and 2A, the prosthesis is generally similar to that shown in FIGS. 1 and 1A, and like reference numerals are used to indicate equivalent components. However, the TKR shown in FIGS. 2 and 2A are intended mainly for revision operations, in which it may be necessary to remove bone, e.g. because of damage caused by the original prosthesis or in extracting it.

The main difference between the embodiment of FIGS. 2 and 2A and FIGS. 1 and 1A is that the tibial bearing component 31 is encased in a tubular outer shell 20. As can be seen, the femoral component is the same as in FIGS. 1 and 1A, but the tibial components comprise a tibial hinge part 8 having a relatively short integral spigot or stem 30. Stem 30 is received in a plastic tibial bearing component 31, within which stem 30 is rotatable to provide a degree of rotational laxity. Component 31 is itself received in a metal shell member 20 having external anti-rotation lugs to ensure that the shell 20 remains stationary with respect to the tibia. Component 31 is prevented from rotation in shell 20 by abutments 100 and 101 which may retain component 31 in shell 20 by a snap fit. At the distal end of the shell 20, a socket 21 is provided for receiving a modular tibial stem 22. Stem 22 may be provided in a range of diameters and lengths to suit the particular patient and is fixed into the socket 21, e.g. by press-fitting or heat-shrinking. Shell component 20 may be manufactured from a suitable metal, e.g. in titanium alloy. In order to take up additional loss of bone in the proximal end of the tibia and to provide the surgeon with means for adjusting the height of the horizontal hinge axis A—A, a spacer 23 may be introduced and which may be a sliding fit over the end of the tibial shell 20. Tibial spacer 23 is formed integrally with anti-rotation lugs 42. These are hollow and are aligned with anti-rotation lugs on shell 20 so that the latter nest in the hollows in lugs 42. Of course, when no spacer plates 23 are present the lugs on shell 20 engage directly in the bone canal. Tibial spacer 23 may be available in a number of different thicknesses to suit particular patients. Similarly, a femoral spacer (23a) may be available in a number of different thicknesses to take up additional loss of bone in the distal end of the femur. Lugs 42a may be provided on spacer 23a to prevent rotation within the bone canal. Lugs 42a are also hollow and lugs on hinge body 3 are aligned with and nest in the hollows of lugs 42a.

In the proximal area of the femoral component 1, there may also be loss of bone and a space filler 24 which may again be formed from suitable biomedically inert plastics material, and moulded in a shape and configuration to suit the patient's characteristics, may be slid over the femoral stem 2 to take up space resulting from revision operation. Similarly, a tibial space filler (24a) may be slid over the shell 20 to take up space resulting from revision operation.

Referring to FIGS. 3 and 3A, these drawings show a further variation of the arrangement shown in FIGS. 1 and 1A. Again, corresponding parts are indicated by the same reference numerals. The embodiment shown in FIGS. 3 and 3A is intended for bone tumour cases where the proximal tibial bone is removed. As can be seen, the femoral component is the same as in FIGS. 1 and 1A, but the tibial components comprise a tibial hinge part 8 having a relatively short integral stem 30. Stem 30 is received in a plastics tibial bearing component 31, within which stem 30 is rotatable to provide a degree of rotational laxity. Component 31 is itself received in a body member 32 which is shaped to replace the upper end of the tibia. Body member 32 incorporates a recess 33 into which a modular tibial stem extension 34 is a press-fit and includes a suture hole 35.

Finally, FIGS. 4 and 4A show a further variation of the embodiment shown in FIGS. 1 and 1A. In this embodiment, the tibial part of the prosthesis is essentially the same as that shown in FIGS. 1 and 1A or FIGS. 2 and 2A. However, the femoral portion has been modified to deal with bone tumour cases affecting the distal part of the femur. Thus, the femoral hinge part 3 and the patella flange are formed as a unitary body member 40, e.g. as a casting. The femoral body member 40 may be formed with a blind bore to receive a femoral stem 2 of desired length, diameter and profile to suit the particular patient. The stem may be press-fitted into the body member 40.

For ease of guiding the femoral or tibial stem into an intramedullary canal, a mushroom-shaped button 51 (e.g. made from an acrylic polymer) may be attached to the tip of stem 2 (see all Figures). The diameter of the button is chosen to be slightly wider than the tip of the stem. The button prevents the stem straying from the centre line of the canal during insertion by the surgeon.

I claim:

1. A total knee replacement prosthesis (TKR), comprising:
   (a) a tibial component having a stem received in a tubular bearing component of plastics material adapted to be inserted in an intramedullary canal of a tibia, the stem being rotatable within said bearing component to provide a degree of rotational laxity for the TKR;
   (b) a femoral component comprising a femoral stem adapted to be fixed in an intramedullary canal of a femur;
   (c) a pin for hingedly connecting said tibial component and said femoral component, the pin defining a lateral-medial hinge axis, the tibial component comprising an upper tibial plate portion and a pair of tibial ear portions at opposite ends of said plate portion, and said femoral component comprising a tubular body portion dimensioned to fit between said tibial ear portions and having a bore therethrough to receive said hinge pin, said hinge pin having opposite ends received in apertures pierced in said tibial ear portions, thereby forming a hinge permitting pivoting of said femoral and tibial components about said medial-lateral hinge axis, wherein the bearing component has a dished upper end, the tibial component having a corresponding convexly curved lower surface which is received by the dished upper end of the bearing component, whereby the tibial component tends to return to a position in which the hinge pin extends in a lateral-medial direction after removal of a rotational force; and (d) a plastic bumper insert extending between said tibial ear portions and adapted to contact and arrest said femoral body portion at points of extreme flexion and extension.

2. A TKR as claimed in claim 1, wherein the femoral stem is attached to the femoral body portion.

3. A TKR as claimed in claim 1, wherein said hinge pin is fixed in said apertures in said tibial ears and rotates in plastics bushes in the bore of the femoral body portion.

4. A TKR as claimed in claim 1, wherein the bearing component is adapted to be non-rotationally fixed in the tibial intramedullary canal.

5. A TKR as claimed in claim 1, wherein a space filler component is received over the femoral stem to compensate for bone loss in the proximal femoral region.

6. A TKR as claimed in claim 1, wherein the bearing component is received within a shell component which is adapted to be fixed to a tibia, said shell component having attachment means at a distal end of said shell component for attaching a tibial stem extension.

7. A TKR as claimed in claim 6, wherein said shell component is tubular.

8. A TKR as claimed in claim 6, wherein the shell component is shaped to compensate for proximal tibial bone loss.

9. A TKR as claimed in claim 1, wherein said plastics bumper insert is snap fit in a recess in said tibial plate portion.

10. A TKR as claimed in claim 1, wherein the femoral component is shaped to compensate for proximal femoral bone loss.

11. A TKR as recited in claim 1, wherein a space filler component is received over the tibial stem to compensate for bone loss in the proximal tibial region.

* * * * *